United States Patent [19]
Thwaites

[11] Patent Number: 5,592,934
[45] Date of Patent: Jan. 14, 1997

[54] ANAESTHETIC VAPORIZER

[75] Inventor: David J. Thwaites, Addingham, England

[73] Assignee: The BOC Group plc, Windlesham, England

[21] Appl. No.: 264,112

[22] Filed: Jun. 22, 1994

Related U.S. Application Data

[63] Continuation of Ser. No. 737,858, Jul. 30, 1991, abandoned.

[30] Foreign Application Priority Data

Aug. 2, 1990 [GB] United Kingdom .................. 9016970
Apr. 26, 1991 [GB] United Kingdom .................. 9109022

[51] Int. Cl.⁶ .................................................. A61M 15/00
[52] U.S. Cl. ............................ 128/203.12; 128/203.14; 128/203.25
[58] Field of Search ........................ 128/202.22, 203.12, 128/203.25, 204.13, 204.22, 203.26, 203.27, 203.14

[56] References Cited

U.S. PATENT DOCUMENTS

| | | | |
|---|---|---|---|
| 3,251,361 | 5/1966 | Rusz | 128/202.22 |
| 3,351,057 | 11/1967 | Goodyear et al. | 128/202.22 |
| 3,741,208 | 6/1973 | Jonsson et al. | 128/202.22 |
| 4,191,952 | 3/1980 | Schreiber et al. | 128/202.22 |
| 4,442,856 | 4/1984 | Betz | 128/202.22 |
| 4,466,433 | 8/1984 | Robbins | 128/202.22 |
| 4,474,175 | 10/1984 | Hudimac, Jr. | 128/202.22 |
| 4,484,576 | 11/1984 | Albarda | 128/202.22 |
| 4,587,966 | 5/1986 | Albarda | 128/202.22 |
| 4,693,853 | 9/1987 | Falb et al. | 128/203.25 |
| 4,798,689 | 1/1989 | Heim et al. | 261/39.1 |
| 5,146,915 | 9/1992 | Montgomery | 128/203.26 |

FOREIGN PATENT DOCUMENTS

| | | |
|---|---|---|
| 0039932 | 11/1981 | European Pat. Off. . |
| 71838 | 3/1970 | Germany . |
| 1224478 | 3/1971 | United Kingdom . |
| 2148721 | 6/1985 | United Kingdom . |
| 2216807 | 10/1989 | United Kingdom . |

*Primary Examiner*—Aaron J. Lewis
*Attorney, Agent, or Firm*—Roger M. Rathbun; Larry R. Cassett; R. Hain Swope

[57] ABSTRACT

An anesthetic vaporizer is disclosed having an inlet for receiving carrier gas and an outlet for delivering carrier gas with an anesthetic agent to a patient. The vaporizer has a passage that extends between the inlet and the outlet, a vaporizing chamber and a passageway extending from the vaporizing chamber to the outlet. A means such as a differential pressure transducer monitors the differences in pressure between the carrier gas in the passage and the anesthetic agent in the passageway to control the flow of the anesthetic agent through the passageway.

10 Claims, 7 Drawing Sheets

ANAESTHETIC VAPORIZER

This is a continuation of application Ser. No. 07/737,858 filed Jul. 30, 1991, now abandoned.

The present invention relates to an anaesthetic vaporiser.

An anaesthetic vaporiser of the by-pass type is disclosed in GB-1224478. In that vaporiser, a carrier gas such as oxygen, air or nitrous oxide is initially divided on entry to the vaporiser between a first stream which is directed towards the sump or vaporising chamber of the vaporiser to entrain vapour from a volatile liquid anaesthetic agent contained therein, and a second by-pass stream, the first and second stream subsequently recombining prior to leaving the vaporiser for delivery to a patient. The rate at which the agent is supplied to the patient is affected by, amongst other things, the rate of flow of gas in the first stream.

This known vaporiser has been used successfully for a considerable period of time for delivering anaesthetic agents such as halothane, trichloroethylene and ether derivatives including enflurane, fluoroxene, methoxyflurane and isoflurane. Such anaesthetic agents generally have a boiling point at normal atmospheric pressure well in excess of 40° C.

A new anaesthetic agent, 2-(difluoromethoxy)-1,1,1,2-tetrafluoroethane, has been developed which as a boiling point at normal atmospheric pressure of about 20° to 25° C. This physical characteristic makes vaporisers of the type disclosed in GB-1224478 unsuitable for delivering 2-(difluoromethoxy)-1,1,1,2-tetrafluoroethane to a patient, since the boiling point is approximately in the middle of the normal operating temperature range of such a vaporiser, which is generally about 15° to 35° C. When the ambient temperature, and hence the vaporiser temperature, is above 25° C., heat is transferred to the low boiling point anaesthetic agent and causes an amount of the agent to vaporise until the heat lost to the latent heat of vaporisation is equal to the heat transferred to the agent.

The present invention provides an anaesthetic vaporiser which can be used to deliver an accurately controlled quantity of an anaesthetic agent to a patient dependent on the vapour pressure of the agent.

According, in one aspect, the invention provides an anaesthetic vaporiser which comprises:

(a) an inlet for carrier gas:

(b) an outlet for the carrier gas and an anaesthetic agent, for deli very to a patient;

(c) a passage which extends between the inlet and the outlet;

(d) a vaporising chamber for an anaesthetic agent;

(e) a passageway which extends from the vaporising chamber to the outlet;

(f) means for monitoring differences in pressure between the carrier gas in the passage and the agent in the passageway;

(g) means for generating a signal corresponding to the pressure difference measured by the pressure difference monitoring means; and (h) a flow control valve located in the passageway for controlling the rate of flow of the agent through the passageway, the valve being controlled by the signal from the pressure monitoring means.

The vaporiser of the present invention will generally include a first restrictor in the passage between the inlet and the outlet, and a second restrictor in the passageway between the flow control valve and the outlet. One of these restrictors, generally the second restrictor, will be adjustable. This can allow the concentration of the anaesthetic agent in the carrier gas, and hence the quantity of anaesthetic agent supplied to the patient, to be adjusted according to requirements.

The restrictors will generally be laminar flow restrictors so that turbulence in the passage, over a range of pressures, is minimised.

The vaporiser of the present invention has the significant advantage that the quantity of the anaesthetic agent supplied to a patient is very significantly less dependent on the vapour pressure of the agent. This allows the vaporiser of the present invention to be used to deliver an anaesthetic agent to a patient, which has a boiling point in the region of the operating temperature range of the vaporiser. An example of such an anaesthetic agent is 2-(difluoromethoxy)-1,1,1,2-tetrafluoethane. However, the vaporiser of the invention may also be used for delivery of anaesthetic agents whose boiling point is removed from the normal operating temperature range of the vaporiser, this flexibility being a particular advantage of the vaporizer.

The pressure difference monitoring means may comprise, for example, a differential pressure transducer. Such a transducer may comprise two chambers which are separated by a flexible membrane, the pressure difference being measured across the membrane.

The pressure difference monitoring means might comprise a differential pressure switch.

The vaporiser may include valves to control the flow of carrier gas or of anaesthetic agent or both in the event of failure of a component of the vaporiser. For example, a valve may be provided to prevent flow of anaesthetic agent from the vaporising chamber. Such a valve will be opened in the normal operating condition of the vaporiser.

A passage may be provided through which carrier gas or anaesthetic agent or both might flow past the pressure difference monitoring means, flow of fluid through the said passage being controlled by a valve. Under normal operating conditions of the vaporiser, such a valve will be closed. However, in the event of failure of a component of the equipment it can be useful to open such a valve to provide a relief passage for flow of the gas or agent, as required.

Preferably, the vaporiser includes a safety control device by which safety valves are operated. They may be operated in response to, for example, the detection of a low anaesthetic agent level in the vaporising chamber, an abnormal pressure in the passage or in the passageway or both, an abnormal temperature especially in the vaporising chamber or the passageway, a power failure, abnormal movement or positioning (for example tilting), and so on. In such failure or otherwise abnormal operating conditions, a valve controlling flow of anaesthetic agent out of the vaporising chamber will generally be closed.

The safety control device is preferably connected to a manually variable restrictor positioned in the passageway between the flow control valve and the outlet, in such a way that addressing the condition detected by the control device is possible only after the variable restrictor has been set to the position at which flow of the anaesthetic agent is at zero.

The vaporiser may include means for controlling the temperature of drug contained within the vaporising chamber. For example, this might be a source of heat from which heat can be supplied to cause vaporisation of the agent. In this way, the temperature of the anaesthetic agent within the vaporising chamber can be maintained at a desired level relative to its boiling point, thereby minimising variations in vapour pressure with the surrounding temperature encountered by the vaporiser. This has the particular advantage of making it possible to use the vaporiser of the invention to deliver anaesthetic agents whose boiling points are significantly above normal ambient temperatures.

The vaporiser of the invention may be provided with means for monitoring the vapour pressure of the anaesthetic agent so that the temperature of the liquid agent can be adjusted to maintain its vapour pressure at a predetermined level.

Instead of, or in addition to, a source of heat, cooling means may be provided associated with the vaporising chamber, again to maintain the temperature of anaesthetic agent within the chamber at a predetermined level relative to its boiling point, or to maintain the vapour pressure of the agent at a predetermined level.

A source of heat may be provided in the passageway between the vaporising chamber and the outlet, in order to minimise condensation of anaesthetic agent during flow through the passageway.

Preferably, the vaporiser of the invention includes means by which leaks, for example, in the passage or the passageway, can be detected. Preferably, such leaks are detected by monitoring the way in which pressure within one or more components of the vaporiser changes with time. To facilitate detection of a leak in this way, the vaporiser may include means for applying a pressure difference between carrier gas in the passage and anaesthetic vapour in the passageway. For example, a piston may be included by which the pressure of the carrier gas wall of the anaesthetic agent may be increased (or decreased). The subsequent change in the pressure difference between the carrier gas and the anaesthetic agent can then be monitored; if there is a leak in a component of the vaporiser, this will be apparent from the way in which the pressure difference changes with time. It will generally be desirable for the change in pressure introduced by the piston to be measured accurately. This can be achieved, for example, by operating the piston pneumatically or electrically.

Leaks within the vaporiser, especially within the pressure difference monitoring means (as can occur in a diaphragm in a differential pressure transducer) can be detected by isolating the pressure difference monitoring means from the carrier gas supply or from the vaporising chamber, and monitoring the change in pressure across the monitoring means. To this end, the vaporiser may be provided with one or more valves to allow it to be isolated from one or each of the carrier gas and the anaesthetic agent, and a vent associated with the or each such valve to allow pressure within the monitoring means to drop. Preferably, two such valves with associated vents are provided, to allow leaks in the monitoring means and in each arm of the flow system to be detected.

Preferably, the vaporiser enables the pressure difference monitoring means to be calibrated, to ensure that a zero pressure difference is accurately measured. The vaporiser may include a passageway by which the pressure difference monitoring means can be connected to a single pressure source, for example to atmospheric pressure or to the carrier gas pressure or to the anaesthetic agent pressure. Alternatively, or in addition, the vaporiser may include a port by which the pressure difference monitoring means can be connected to a single pressure source. The port may be one which is provided for connection of the pressure difference monitoring means to the carrier gas pressure or to the anaesthetic agent pressure, so that the connection of the monitoring means to a single pressure source simply involves disconnection from the carrier gas and the anaesthetic agent.

The calibration of the pressure difference monitoring means may be determined alternatively by providing more than one pressure difference monitoring means, and comparing the pressure difference monitored by the respective monitoring means. In the event that the readings from the monitoring means differ, recalibration of one or each of the monitoring means is likely to be appropriate.

Embodiments of the invention will now be described by way of example with reference to the accompanying drawings, in which.

Figure 1:
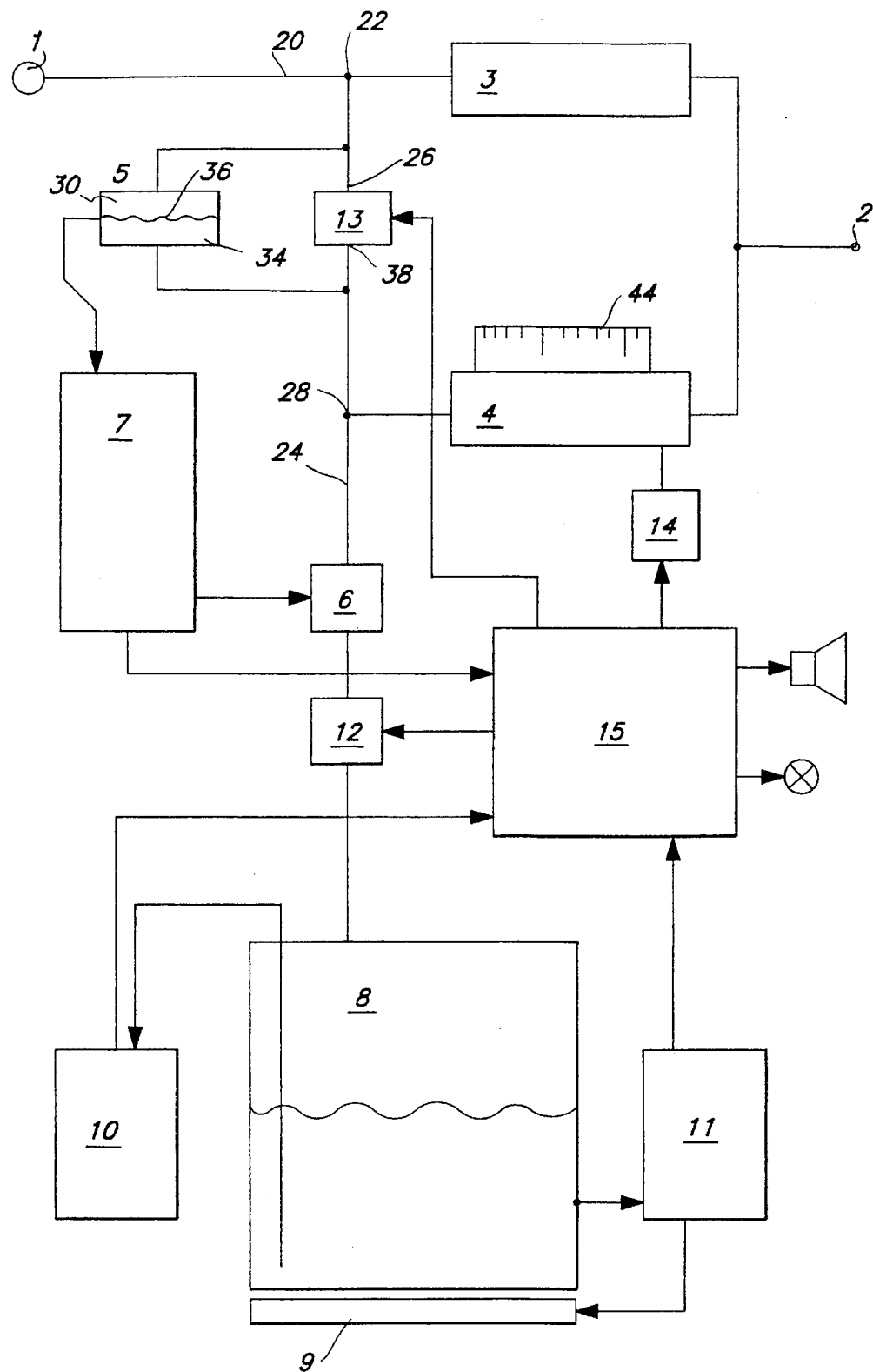
FIG. 1 is a schematic illustration of an anaesthetic vaporiser.

Referring to the drawings, FIG. 1 shows an anaesthetic vaporiser which has an inlet 1 for carrier gas and an outlet 2 for a controlled mixture of carrier gas and gaseous anaesthetic agent. Extending between the inlet 1 and the outlet 2 is a passage 20 in which is located a fixed laminar flow restrictor 3. The restrictor 3 exhibits laminar flow characteristics over its operating range.

A second passage 24 extends from a vaporising chamber 8 containing liquid anaesthetic agent such as 2-(difluoromethoxy)-1,1,1,2-tetrafluoroethane to he outlet 2. Located in the passage 24 between the vaporising chamber 8 and the outlet 2 in a manually variable laminar control valve 4 including an adjustable dial 44 known per se.

Also located in the passage 24 is an electrically operated flow control valve 6 and a vaporising chamber shut-off valve 12 which is held open during normal operation of the anaesthetic vaporiser.

The passage 20 communicates at point 22 with one chamber 30 of a differential pressure transducer 5 and with one side 26 of a transducer by-pass valve 13. Similarly, passage 24 communicates at point 28 with a second chamber 34 of the differential pressure transducer 5 and with the other side 38 of the transducer by-pass valve 13 is held closed during normal operation of the anaesthetic vaporiser.

The control valve 6 is electrically connected to a device 7 which receives electrical signals from the pressure transducer 5 and subject to said signals continuously controls the setting of the control valve 6.

Associated with the vaporising chamber 8 is a heater 9, a temperature control system 11 and an anaesthetic agent level sensing device 10.

Linked to the control valve 4 is a solenoid dial interlock 14 which is normally powered to allow rotation of the dial 44 of the manually variable laminar control valve.

As illustrated a centralised alarm system 15 is provided which is electrically linked with the vaporising chamber shut-off valve 12, the transducer by-pass valve 13, the solenoid dial interlock 14, the vaporising chamber temperature control system 11, the fluid anaesthetic agent level sensing system 10 and the device 7.

In use, fresh carrier gas is fed to the inlet 1 of the vaporiser from a conventional flow metering bank delivering typically 0.2 to 15 liters per minute of air, oxygen and nitrous oxide in various proportions.

The carrier gas passes along the passage 20 through the fixed restrictor 3 towards the outlet 2. The pressure of the carrier gas at point 22 upstream of the restrictor 3 is transmitted to the first chamber 30 of the differential pressure transducer 5.

As previously, stated during normal operation the transducer by-pass valve 13 is closed.

Simultaneously, heat from the heater 9 will raise the temperature of the liquid anaesthetic agent in the vaporising chamber 8 and vapour will then pass through passage 24, through the shut-off valve 12 which, in normal use, is held open, through the electrically operated flow control valve 6 and the manually variable laminar control valve 4 to join with the carrier gas prior to leaving the vaporiser at the outlet 2.

The pressure of the vapour at point 28 upstream of the control valve 4 will be communicated to the second chamber 34 of the pressure transducer 5. The differential pressure transducer emits an electrical signal dependent on the differential between the carrier gas pressure and the agent vapour pressure which is transmitted to the device 7 which passes a signal which controls the setting of the flow control valve 6. The differential pressure transducer 5, the device 7 and the electrically operated flow control valve 6 between them form an active regulator which operates to balance exactly the pressure of agent vapour at the inlet to the manually variable restrictor 4 with the pressure of fresh carrier gas at the inlet to the fixed restrictor 3.

Thereafter, for a given carrier gas make-up and particular agent vapour the volume for volume ratio of vaporised agent to carrier gas depends almost wholly on the position of the manually variable valve 4 and is substantially independent of the carrier gas flow rate.

All alarm conditions that arise will cause the vaporising chamber shut-off valve 12 to close and audible/visual alarms to operate. The alarm is preferably designed so that it can only be acknowledged by rotating the manually variable restrictor dial 44 to "off" where the control dial rotation becomes interlocked and the vaporiser isolated.

An advantage of the vaporiser shown in FIG. 1 is that nearly all alarm conditions result in the inability of the device 7 to maintain a differential pressure of zero. The condition is readily monitored by the control electronics and simplifies alarm handling.

It will be evidence that automatic zeroing of the pressure transducer 5 is possible by the occasional operation of he transducer by-pass valve 13.

Figure 2:
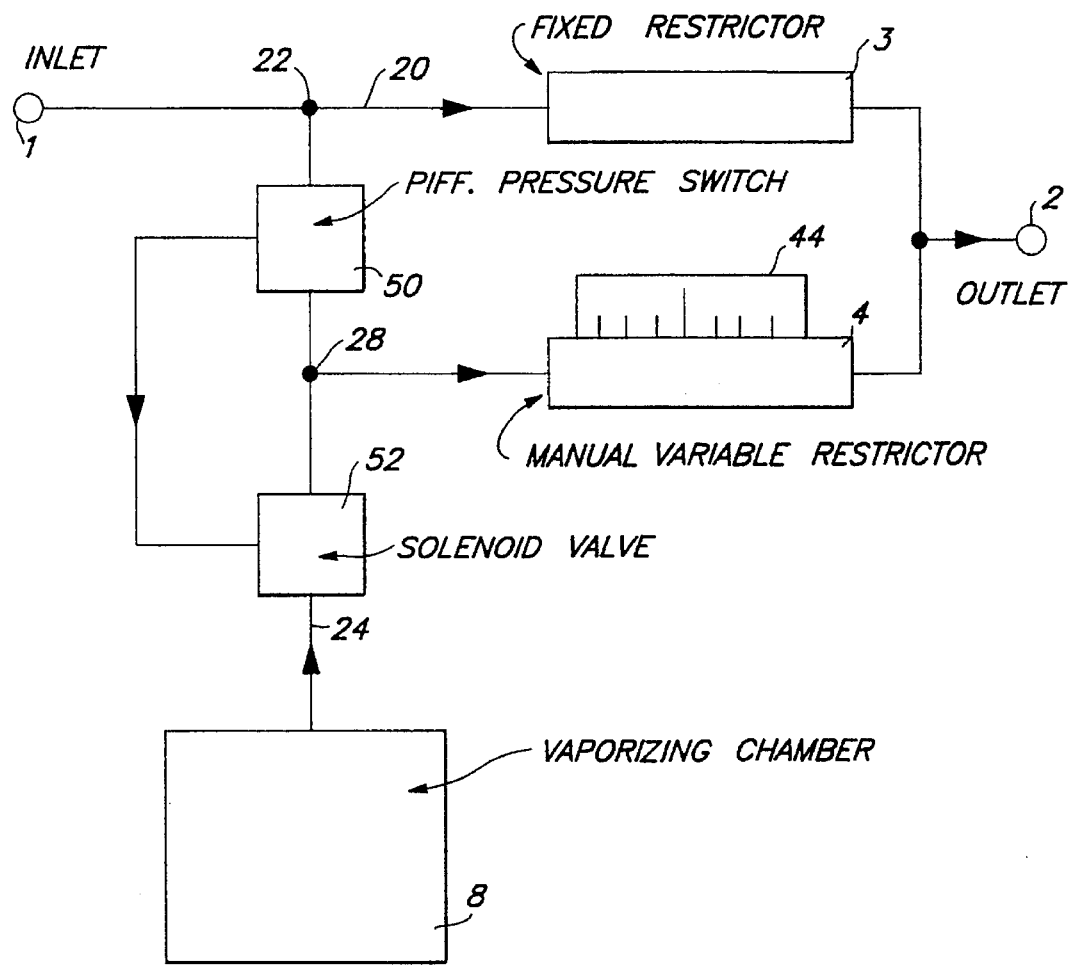
FIG. 2 is a schematic illustration of another embodiment of vaporiser.

Referring now to FIG. 2, there is illustrated an anaesthetic vaporiser which is a modification of the anaesthetic vaporiser referred to with reference to FIG. 1. In FIG. 2, like reference numerals denote similar features as referred to with reference to FIG. 1.

As shown in FIG. 2, an anaesthetic vaporiser has an inlet 1 for carrier gas and an outlet 2 for a controlled mixture of carrier gas and gaseous anaesthetic agent. Extending between the inlet 1 and the outlet 2 is a passage 20 in which is located a fixed laminar restrictor 3.

A second passage 24 extends from a vaporising chamber 8 to the outlet 2. Located in passage 24 is a manually variable laminar flow control valve 4 including an adjustable dial 44.

A differential pressure switch 50 is located between a point 22 in the passage 20 and a point 28 in the passage 24.

Also located in the passage 24 is a solenoid valve 52.

Signals from the differential pressure switch 50 are arranged to operate the solenoid valve 52.

In use, fresh carrier gas is fed to the inlet 1 and flows through passage 20 and fixed restrictor 3 towards the outlet 2. The pressure of the carrier gas at point 22 upstream of the fixed restrictor 3 is transmitted to a first side of the differential pressure switch 50.

Simultaneously, heat from a heater (not shown) will raise the temperature of liquid anaesthetic agent in the vaporising chamber 8 and vapour will then pass through solenoid valve 52, passage 24 variable restrictor 4 to join with the carrier gas prior to leaving the vaporiser at the outlet 2.

The pressure of the vapour at point 28 upstream of he control valve 4 will be communicated to the opposite side of the differential pressure switch 50. The differential pressure switch 50 will emit an electrical signal dependent on the differential between the carrier gas pressure and the agent vapour pressure which signal is transmitted to the solenoid valve 52.

The volume between the differential pressure switch 50, the solenoid valve 52 and the variable restrictor 4 form a pressure control volume and, the differential pressure switch 50 operates the solenoid valve 52 directly opening it when the inlet pressure of carrier gas exceeds the control volume pressure and closes it when the pressures are equalised.

The operation of the solenoid valve 52 could be arranged such that it is opened regularly, for example, every second and maintained open for a period of up to one second as required to equalise the pressures.

It will be apparent that the modification illustrated in FIGS. 2 of the embodiment described with reference to FIG. 1 is far simpler in that it consists of a pressure switch and solenoid valve which replace the differential pressure transducer, control electronics and flow control valve of the embodiment described with reference to FIG. 1.

Figure 3:
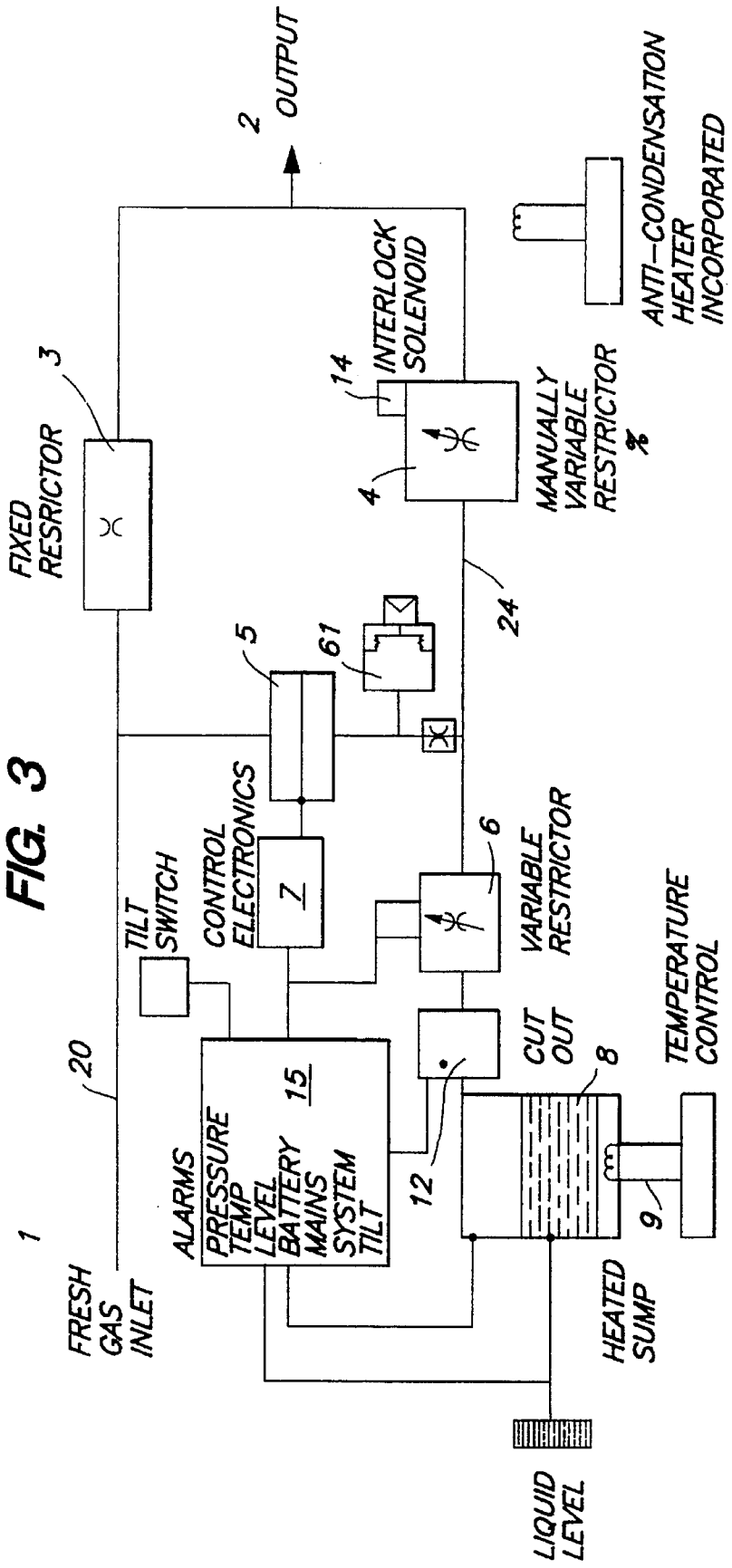
FIGS. 3 and 4 are schematic illustrations of further embodiments of vaporisers, which include leak detection components.

FIG. 3 shows a vaporiser which includes a piston 61 by which a small disturbance in the volume on the anaesthetic agent side of the circuit can be introduced. The piston is operated electrically, by a solenoid device (although it may be operated pneumatically or manually). The disturbance introduced by the piston gives rise to a pressure change across the pressure difference monitoring means 5. The subsequent decay of he measured pressure change can provide a measure of the integrity of the pneumatic circuit in the anaesthetic agent part of the vaporiser circuit and, in particular, in the diaphragm within the differential pressure transducer which forms part of the pressure difference monitoring means.

Figure 4:
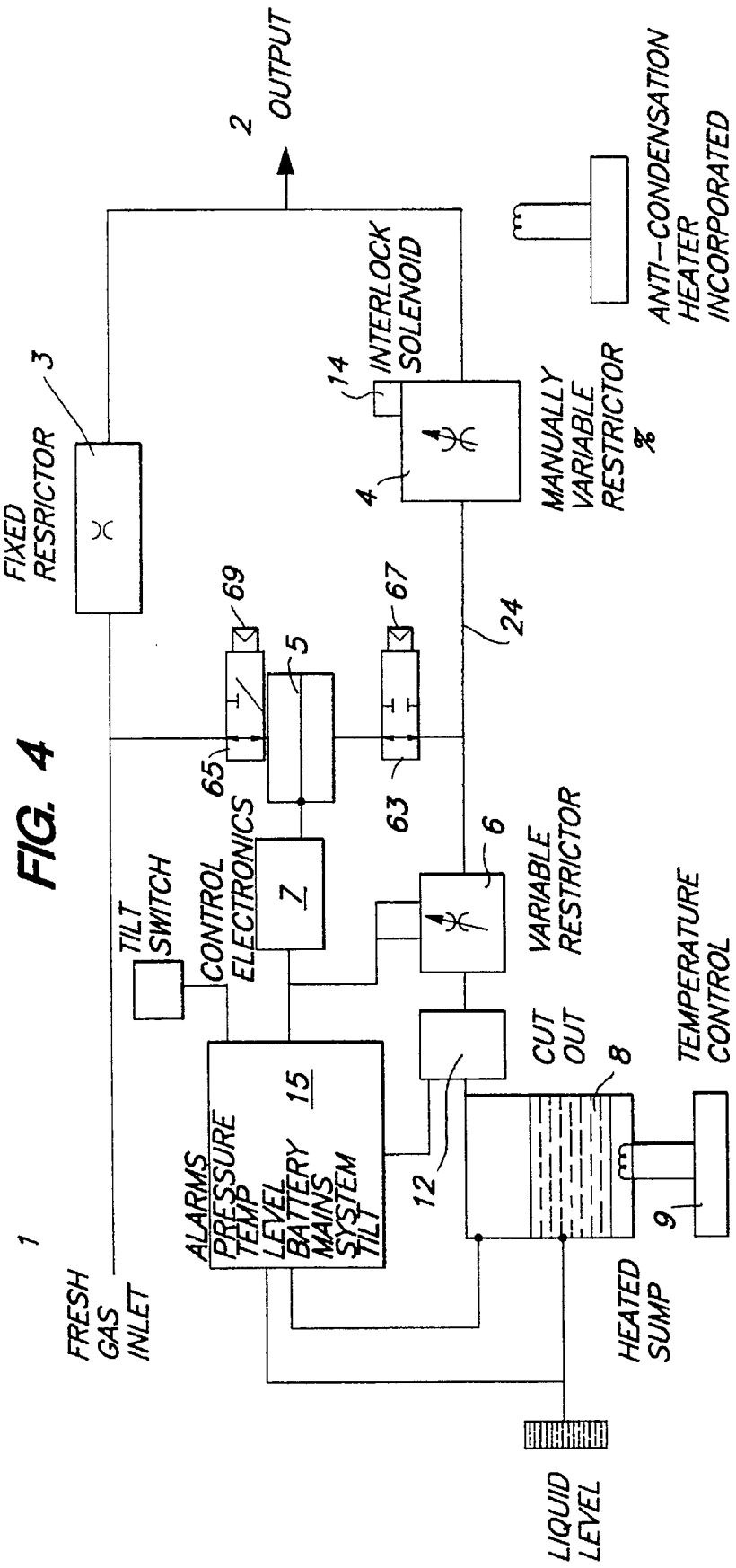

FIG. 4 shows a vaporiser which includes two valves 63, 65 with associated vents 67, 69. Using these valves and vents, the pressure on one side of the transducer 5 can be reduced to atmospheric pressure, and the decay in the pressure difference monitored by the transducer provides a measure of the integrity of the pneumatic circuit and of the transducer diaphragm.

Figure 5:
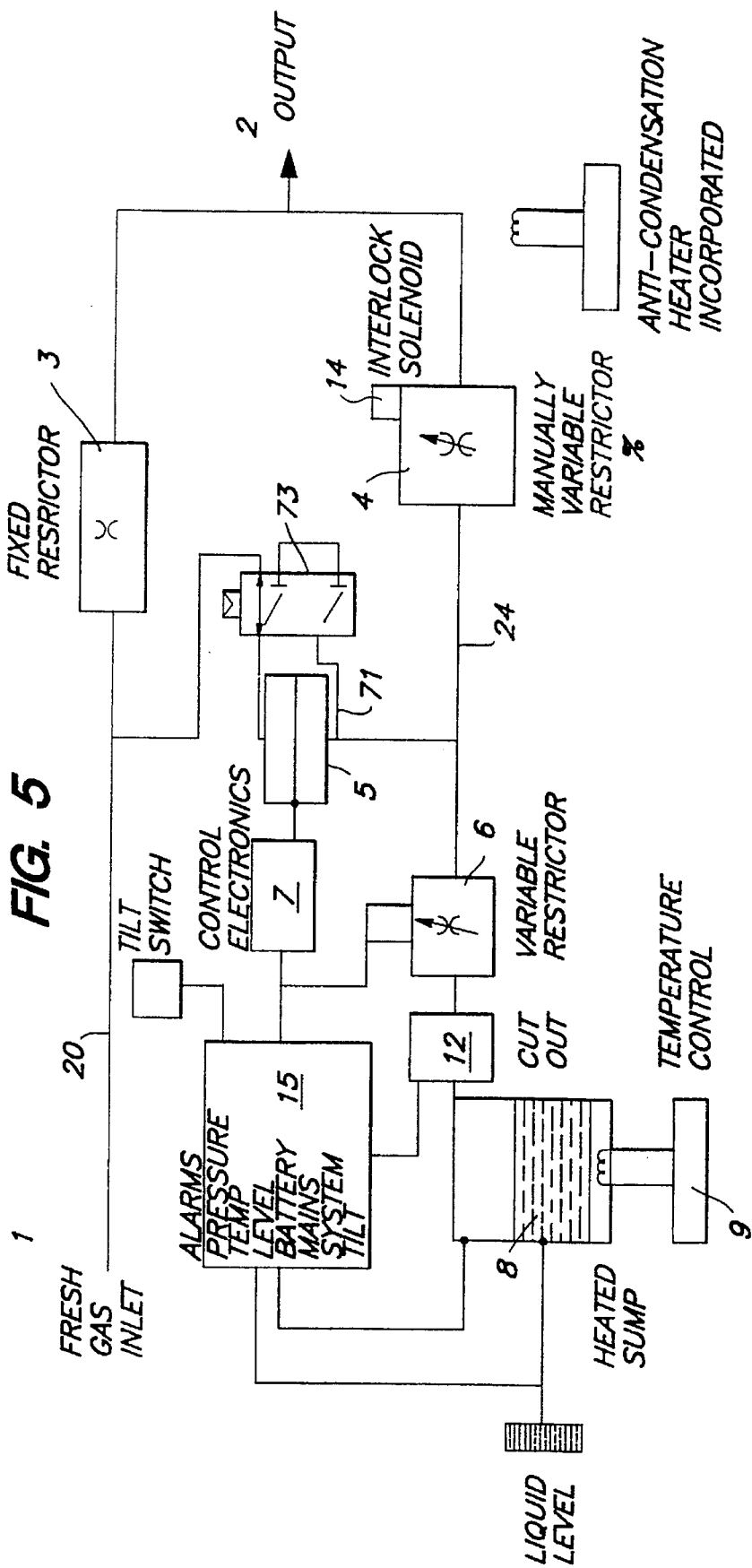
FIGS. 5 to 7 are schematic illustrations of vaporisers which include components for calibration of the pressure difference monitoring means.

FIG. 5 shows an embodiment of vaporiser which includes a passageway 71 with an associated valve 73 which may be switched to allow both sides of the transducer 5 to be connected to one side (which may be the carrier gas side or the anaesthetic agent vapour side) only of the pneumatic circuit. When so connected, the output of the transducer should be zero. If it is not zero, it can be recalibrated appropriately. FIG. 5 shown schematically the arrangement in which both sides of the transducer are connectable to the anaesthetic agent vapour side.

Figure 6:
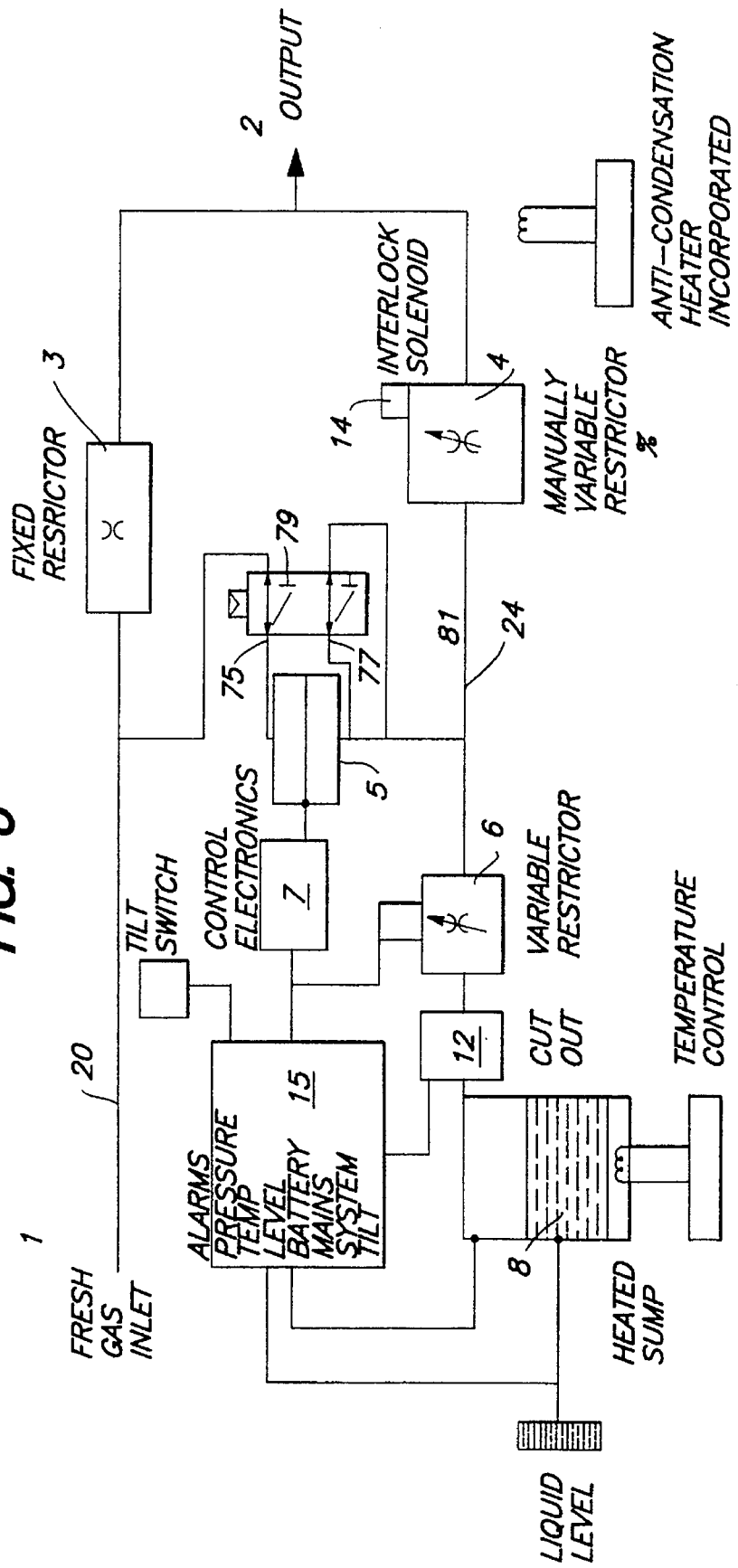

The vaporiser shown in FIG. 6 includes two valves 75, 77, each with associated ports 79, 81, by which each side of the transducer 5 can be exposed directly to ambient pressure. The resulting output of the transducer should then be zero, and can be adjusted appropriately if it is not.

Figure 7:
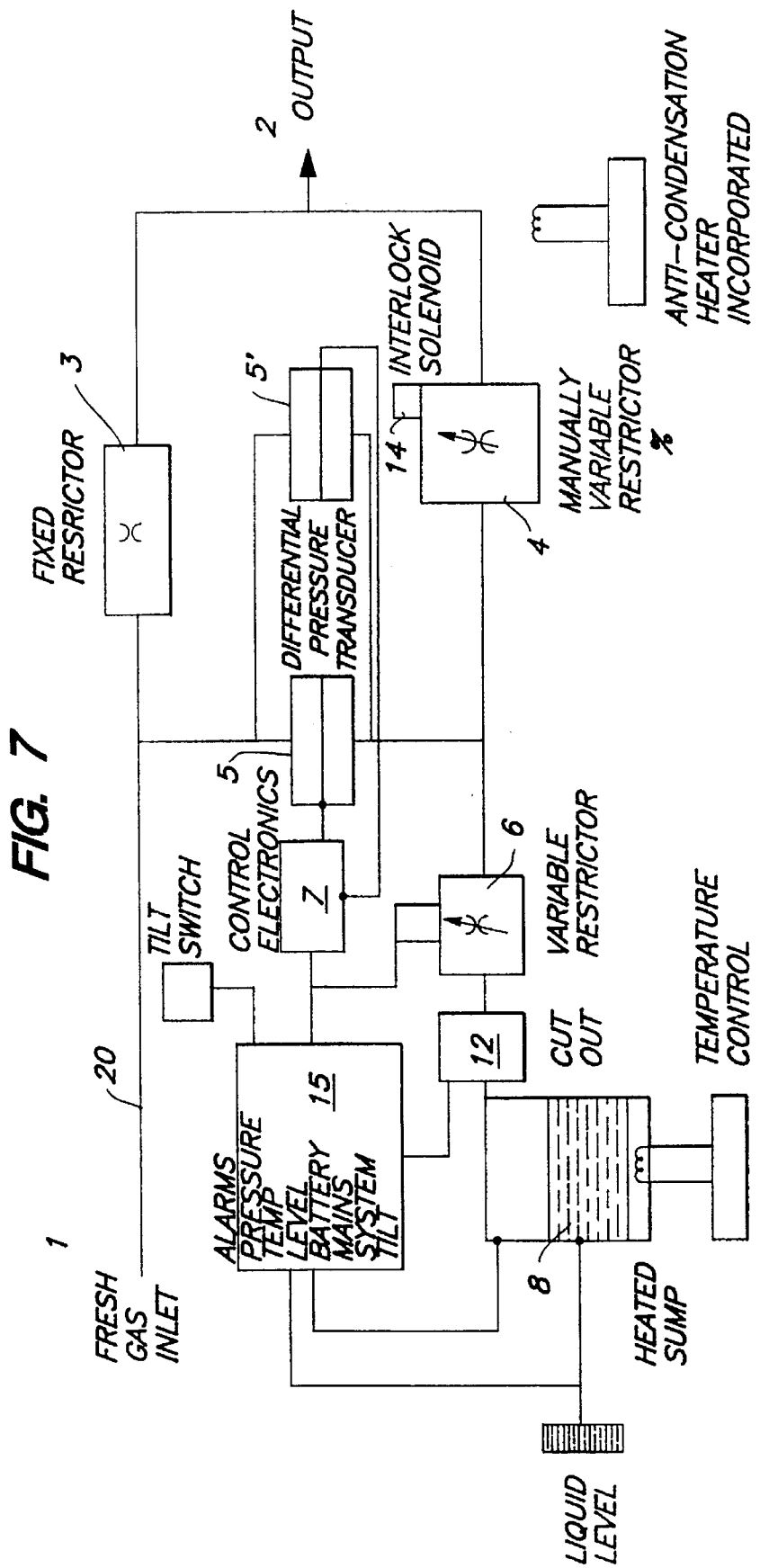

FIG. 7 shows a vaporiser which includes two differential pressure transducers 5,5'. The output from the two pressure transducers can be compared and, in the event that their readings differ, an appropriate adjustment or recalibration can be made.

I claim:

1. An anaesthetic vaporizer which comprises:
   (a) an inlet for carder gas;
   (b) an outlet for the carrier gas and an anaesthetic agent for delivery to a patient;
   (c) a passage which extends between said inlet and said outlet;
   (d) a vaporizing chamber for an anaesthetic agent;
   (e) a passageway which extends from the vaporizing chamber to said outlet;
   (f) a pressure transducer which generates an electrical signal corresponding to the differences in pressure between the carder gas in said passage and the agent in said passageway;
   (g) means for generating an electrical control signal corresponding to the pressure difference measured by said pressure transducer; and
   (h) an electrically operated control valve located in said passageway for controlling the rate of flow of the agent through said passageway, said valve being controlled by the electrical signal from said control signal generating means; and
   (i) further including means for automatically ensuring the isolation of the vaporizing chamber and resetting of the manually adjustable restrictor during an alarm condition.

2. A vaporizer as claimed in claim 1 which includes a restrictor in the passage.

3. A vaporiser as claimed in claim 2 in which the restrictor in the passage is a laminar flow restrictor.

4. A vaporizer as claimed in claim 1 which includes a restrictor in the passageway.

5. A vaporiser as claimed in claim 4 in which the restrictor in the passageway is manually adjustable.

6. A vaporiser as claimed in claim 1 which includes a valve by which flow of anaesthetic agent from the vaporising chamber can be adjusted.

7. A vaporiser as claimed in claim 1 which includes a passage for by-passing the pressure transducer, flow of fluid through the said passage being controlled by a valve.

8. A vaporiser as claimed in claim 7 which includes a safety control device, by which the said valve is controlled.

9. A vaporiser as claimed in claim 8 which includes a manually adjustable restrictor in the passageway, the safety control device being connected to the said retrictor in such a way that addressing the condition detected by the control device is possible only after the variable restrictor has been set to the position at which flow of the anaesthetic agent is at zero.

10. A vaporiser as claimed in claim 9 which includes means for controlling the temperature of the vaporising chamber.

* * * * *